United States Patent
MacWhinnie et al.

(10) Patent No.: US 6,261,313 B1
(45) Date of Patent: *Jul. 17, 2001

(54) C-SHAPED HEAT PACK FOR THERMAL TREATMENT OF BREAST

(76) Inventors: John MacWhinnie; Virginia MacWhinnie, both of 261 Deerfield Rd., Water Mill, NY (US) 11976

( * ) Notice: Subject to any disclaimer, the term of this patent is extended or adjusted under 35 U.S.C. 154(b) by 0 days.

This patent is subject to a terminal disclaimer.

(21) Appl. No.: 09/108,932

(22) Filed: Jul. 1, 1998

Related U.S. Application Data

(63) Continuation of application No. 08/400,860, filed on Mar. 8, 1995, now Pat. No. 5,776,177.

(51) Int. Cl.⁷ .................................................... A61F 7/00
(52) U.S. Cl. .......................................... 607/108; 128/890
(58) Field of Search ..................................... 607/108–110; 128/845, 846, 847, 889, 890

(56) References Cited

U.S. PATENT DOCUMENTS

| Re. 14,024 | 11/1915 | Whitmarsh . | |
|---|---|---|---|
| D. 324,915 | 3/1992 | Wastchak | D24/207 |
| D. 365,399 | 12/1995 | Silver | D24/206 |
| 2,049,723 | 8/1936 | Pomeranz . | |
| 2,298,361 | 10/1942 | Freund . | |
| 2,853,077 | 9/1958 | Hunau . | |
| 2,897,821 | 8/1959 | Lerner . | |
| 3,430,632 | 3/1969 | James et al. . | |
| 3,464,418 | 9/1969 | Silverman . | |
| 3,500,832 | 3/1970 | Nunnery . | |
| 3,780,537 | 12/1973 | Spencer | 62/530 |
| 3,830,676 | 8/1974 | Elkins | 156/289 |
| 3,995,621 | 12/1976 | Fletcher et al. . | |
| 4,044,773 | 8/1977 | Baldwin . | |
| 4,416,281 | 11/1983 | Cooper et al. . | |
| 4,552,149 | 11/1985 | Tatsuki . | |
| 4,756,311 | 7/1988 | Francis . | |
| 4,765,338 | 8/1988 | Turner et al. . | |
| 4,846,176 | 7/1989 | Golden . | |
| 4,920,964 | 5/1990 | Francis . | |
| 5,050,595 | 9/1991 | Krafft . | |
| 5,133,348 | 7/1992 | Mayn . | |
| 5,304,215 | 4/1994 | MacWhinnie | 607/106 |
| 5,476,490 | 12/1995 | Silver | 607/108 |

FOREIGN PATENT DOCUMENTS

| 419448 | 3/1967 | (CH) | A61F/7/04 |
|---|---|---|---|
| 3210178A1 | 9/1983 | (DE) | A61F/7/10 |
| 4141806A1 | 5/1993 | (DE) | A61F/7/02 |
| 0449299A1 | 10/1991 | (EP) | A61F/7/10 |

*Primary Examiner*—Linda C. M. Dvorak
*Assistant Examiner*—R. Kearney
(74) *Attorney, Agent, or Firm*—Alfred M. Walker

(57) ABSTRACT

The present invention relates to a C-shaped thermal heat pack for heating the female breast during post partum nursing and, more particularly, to a thermal heat pack which readily conforms to the contours of different sized female breasts to provide therapeutic heat to an adjacent breast to reduce swelling and irritation. The present invention overcomes the disadvantages of the prior art by providing a bendable thermal heat unit which assumes a cup or cone shape upon application to the breast. The present invention adjusts and conforms to various sizes of the female breasts to which it is to be applied. The present invention provides a layered conformable member with a C-shape having a selected indentation to permit formation of various sized rounded conical cups. A centrally located hole is provided for insertion of a nipple therethrough.

6 Claims, 7 Drawing Sheets

C-SHAPED HEAT PACK FOR THERMAL TREATMENT OF BREAST

This app. is a cont: of Ser. No. 08/400,860 Mar. 8, 1995 U.S. Pat. No. 5,776,177.

This application is based upon Applicant's Disclosure Document No. 327192 dated Mar. 8, 1993.

FIELD OF THE INVENTION

The present invention relates to a sealed, substantially C-shaped thermal heat pack for heating a body part, such as the female breast during postpartum nursing and, more particularly, to a thermal heat pack which readily conforms to the contours of different sized female breasts to provide therapeutic heat to an adjacent breast to reduce swelling and irritation, wherein a centrally located recess is provided for the nipple to extend therethrough. The thermal heat pack can also be used to other protruding body parts such as an elbow, knee, an ankle, etc.

In a further embodiment, the heat pack may be constructed so as to be adaptable to fit over a breast pump, for wear while pumping milk, or may have a centrally located nipple shield.

BACKGROUND OF THE INVENTION

A number of cup shaped thermal heat packs are known in the prior art in which thermal heat is provided through a heat pack to provide a therapeutic heat to the human body. Examples of this type of heat pack are shown in U.S. Pat. No. 5,304,215 of the Applicant's, U.S. Pat. Nos. Re 14,024 of Whitmarsh, 2,298,361 of Freund, 3,500,832 of Nunnery, and 5,050,595 of Krafft.

Moreover, U.S. Pat. No. 3,995,621 of Fletcher discloses a liquid cooled brassiere used with diagnostic mammography. Other brassiere patents in general are disclosed in U.S. Pat. Nos. 2,853,077 of Hunau and 3,430,632 of James.

Heat packs in general are disclosed in U.S. Pat. Nos. 3,780,537 of Spencer and 4,846,176 of Golden. Furthermore, U.S. Pat. No. 3,897,821 of Lerner describes a swimming garment wherein breast shaped cups are formed from flat sheets having V-shaped cuts in the sheets.

U.S. Pat. No. 4,552,149 of Jatsuki describes a cooling implement for the head which includes a skull portion and an alternate chin portion. U.S. Pat. No. 4,416,281 of Cooper describes a refillable oval cooling pack with an in flow tube for use during surgery to cool an organ, such as a heart. U.S. Pat. No. 4,044,773 of Baldwin describes a rectangular equine cooling pack for wrapping around a horse's leg.

Other patents include U.S. Pat. No. 5,133,348 of Mayn, U.S. Pat. No. 3,830,676 of Elkins and U.S. Pat. No. 2,049,723 of Pomeranz. However, Mayn '348 described a refillable heat pack which may leak, and contains a large weight which tends to compress the breast uncomfortably, and Mayn can only be used in a lying, supine position, rendering the user immobile. Elkins '676 and Pomeranz '723 are for placement upon the head and Pomeranz '723 includes a circumferential elastic band to keep it upon the crown of a skull, which elastic band could squeeze a breast uncomfortably. Moreover, Pomeranz '723 and Elkins '676 are refillable, and therefore prone to leakage.

These patents are incorporated by reference herein for teaching devices in which heat packs are provided for therapeutic use or otherwise.

With the exception of the heat pack described in Applicants' U.S. Pat. No. 5,304,215 of Apr. 19, 1994, the above prior art devices have many disadvantages. Typically the devices include cup shaped portions which do not conform closely to various sizes of the breast. If the heat pack does not snugly fit the breast once in position, the heat pack may be too tight or too loose to optimize heating resulting in uneven application of heat to the breast.

OBJECTS OF THE INVENTION

It is therefore an object of the present invention to provide a heat pack for a protruding body part, such as a breast, which heat pack comfortably conforms to the shape of the body part.

It is a further object to provide a heat pack for a breast which is lightweight and versatile to use.

It is yet another object to provide a heat pack for a breast which applies heat evenly to the breast.

It is yet another object to provide a heat pack for a breast which provides a recess for a nipple to extend therethrough.

It is yet another object to provide a heat pack which can be used for a variety of protruding body parts.

It is yet another object to improve over the disadvantages of the prior art.

SUMMARY OF THE INVENTION

The present invention overcomes the disadvantages of the prior art by providing a bendable thermal heat unit which assumes a cup or rounded cone shape upon application to a protruding body part, such as a breast or, elbow or a shoulder. The present invention adjusts and conforms to various sizes of the female breasts to which it is to be applied by providing a layered C-shaped conformable member to permit formation of various sized rounded conical cups.

Thus the present invention overcomes the disadvantages of the prior art by providing a thermal heat pack unit which conforms to the contour of various sizes and shapes of the female breast.

Although the Freund '361, Nunnery '832 and Krafft '595 prior art thermal pack units provide cup shaped heat packs, the prior art devices do not increase or decrease in size to accommodate, adjust or conform to various sized breasts. With all of the prior art, it is necessary to provide various sizes of specific heat packs to include the wide range of female breast sizes. Consequently, a large variety of different sizes must be provided so that a user can select a size which will fit a particular breast. With the present adjustable invention, however, one size fits all.

The C-shaped heat pack of the present invention overcomes the disadvantages of the prior art and provides a simple, pliable, light-weight thermal heat pack which readily conforms to the contours of any sized female breast to provide therapeutic heat or cold to the adjacent breast areas.

To further ensure comfort, the heat pack may alternately have a centrally located recess hole for the nipple to extend therethrough.

The heat conductive material may be a heat conductive medium, or a cooling medium.

In the preferred embodiment, the heat conductive material includes a conventional heat conductive medium within a pliable outer material. The outer material is fixed about its perimeter to an adjacent conductive material, so that the heat pack directly contacts with the female breast. This provides for an efficient heat transfer between the thermal heat pack and the female breast.

In addition to containing the heating medium fluid, the present invention also acts to cover the adjacent skin portions of various sized breasts.

The thermal heat pack of the present invention uses conventional thermal gel to heat the pliant flattened C-shaped member which changes form and corresponds to the form of the female breast being covered, as it flexes over the surfaces of the breast.

Moreover, the present invention provides a thermal pack capable of supplying hot or cold temperatures. The thermal pack readily adjusts and conforms to the contours of various sized female breasts to therapeutically heat or cool adjacent skin areas of the breast. The thermal pack has a conforming member which is substantially C-shaped and which has an internal cavity for containing a heat retentive and conductive material.

The heat retaining heat conductive material is flexible, preferably a gel which can be primarily liquid in nature or primarily solid in nature, and which, due to its flexibility as a gel, can be adapted to conform to any sized contour of the female breast. Heat retentive heat conductive gels are conventional and are well known in the art of medical thermal pack appliances.

The heat conductive material may conduct heat either toward the breast skin surface, wherein the breast is warmed, or may conduct heat away from the breast skin surface, wherein the breast is cooled.

Further, the substantially C-shaped conformable member may alternately be provided with a generally centrally located recess and with alternately at least one selectively positioned indentation leading to the recess, which permits the C-shaped member in its non-use flattened form to flex mechanically and thus to assume a cup shape when put into use. In this manner the C-shaped conformable member is able to adjust and conform to various sized female breasts.

The indentation, which permits the mechanical flexing of the C-shaped conformable member, may be a cut made into the outer side of the C-shaped conformable member, which outer side assumes a generally convex shape when the C-shaped conformable member is applied to a female breast. In contrast, when the conformable member is applied to a female breast, the inner side of the conformable member assumes a generally concave shape.

The indentation may begin at the outer or inner side and extend generally into the recess of the C-shaped conformable member without extending all the way therethrough.

Wherein a web connects the sides of the indentation, the relative depth of the recess or the indentation may vary, depending upon the nature, strength and natural flexibility of the unindented material selected for use in constructing the C-shaped conformable member. The more naturally flexible the material selected, the shallower may be the indentation. Conversely, where a material for the C-shaped conformable member is relatively less flexible, the indentation will have to be made deeper, which means that the indentation will have to more closely approximate a cut which would run completely through the C-shaped conformable member from the outer side to the inner side, or from the inner side to the outer side.

The indentation to the central recess may be curved or straight or alternatively may also have a handle appendage opposite the indentation.

Those skilled in the art will appreciate that many varieties of indentation, scoring, notching or otherwise providing for material movement of a flat surface to permit such surface to form a cup shape will be effective in making and using the present invention.

Further, the thermal pack may provide a moist heat conductive foundation surface, such as terry cloth, separating the conforming member from the breast. The terry cloth or other heat conductive foundation is moistened with water when use to heat the breast but not when used to cool the breast. The water-permeated terry cloth, disposed between the breast skin and the conforming member, serves to conduct heat from the surface of the conforming member toward the breast. The heat source is the heat retentive heat conducting gel housed within a cavity in the C-shaped conforming member.

In another embodiment, the thermal heat pack may have no attached moist heat conductive surface, but rather may be insertable within a separate moist heat conductive ferrule sheath.

Further, the moist heat conductive foundation surface, exemplified by but not limited to terry cloth, serves to provide the user of the thermal pack with a comfortable surface for contact with the skin and further to provide the thermal pack with an acceptable appearance whether moisture is applied by the user or not.

The heat retentive and heat conductive material may be one of a variety of conventional thermal gel materials or conventional thermal rubber-like flexible solids all of which are well known in the art of medical thermal packs.

This factor allows the heat pack to become a cup shape in order to conform to the breast. Preferably, the thermal material is a solid gel, not a liquid as found in the previous art. It is the solid gel itself which is formed with the indentation in order to allow sufficient flexibility for maximum conformability to the female breast.

The above method has never appeared in any prior art, and is a unique method for the application of a particular thermal material. Although the thermal material remains as essentially a form of gel, it is not similar to the common liquid gel, in that it is a solid gel with pliant capabilities.

Both forms of gel have equal thermal value, but each form contains characteristics which lead to conformability solutions which are applicable only to that particular medium.

The C-shaped conformable member with a centrally located nipple hole houses the heat retentive heat conductive gel in a cavity within the C-shaped conformable member. The C-shaped conformable member is pliant and flexes from a substantially flat shape when not in use to a substantially cup shape to conform to the breast being covered.

In the alternative, the C-shaped conformable member may be made from a pliant, gelatinous heat conductive material capable of being cut or molded forming flexible shapes.

The C-shaped conformable member with a centrally located nipple hole is preferably constructed of a pliable material provided with an inner cavity to contain the heat retentive heat conductive gel. The C-shaped conformable member has an inner surface and an outer surface, the inner surface facing toward the user's breast.

The C-shaped conformable member's inner surface is preferably suitably attached to the moist heat conductive foundation surface, as by stitching, but without limitation to the manner in which attachment is achieved. The moist heat conductive foundation surface is thus disposed adjacent to the C-shaped conformable member and covers the inner surface thereof to provide a soft and comfortable facing which comes into contact with the skin of the user's breast.

The pliable material of the C-shaped conformable member may be permeable or impermeable to fluids such as water. Where the thermal gel material selected for a particular embodiment is aqueous in nature or has an aqueous component, it may be desirable to prevent the thermal gel material and/or its aqueous component and/or its liquid component comprised of a liquid other than water from permeating the material of the C-shaped member and thereby leaking in an undesirable fashion. To prevent such leakage, the pliable material of the C-shaped conformable member may be a material selected for liquid-impermeability and for resistance to attack by any component or combination of components of the thermal gel housed therein.

In the alternative, it may be desirable to use a thermal gel material for which water is an essential ingredient, and from which water may normally evaporate. There are conventional thermal gels known in the medical thermal pack art which exemplify this water evaporative characteristic.

In such a case, the pliable material of the C-shaped conformable member may be permeable to fluids such as water. When a substantial amount of water has naturally evaporated from the thermal gel material such water can then be replaced by water soaking the pliable material of the C-shaped conformable member to restore the lost moisture.

However, it is nonetheless possible to employ a thermal gel material which is normally expected to lose moisture through evaporation by sealing it in an impermeable pliable material of the C-shaped conformable member. In such case, the naturally-contained moisture of the thermal gel would never be lost, because evaporation would be entirely prevented by the impermeability of the pliable material of the C-shaped conformable member.

When used to heat the breast, the user may warm the heat retentive heat conductive gel within the conformable member any one of a variety of ways. The preferred method is to soak the conformable C-shaped member in warm water for a few minutes. Such warm water soaking would serve to moisten the moist heat foundation surface as well as to warm the heat retentive heat conductive gel. When the thermal pack of the present invention has been sufficiently warmed, the user would insert it into a conventional brassiere for a period of time, and then remove it for re-warming as desired. Alternatively, the user could manually apply the thermal pack to the breast and hold it in place manually for a desired time period.

When used to cool the breast, the C-shaped thermal pack of the present invention is cooled, as by refrigeration, until a suitably cool temperature is achieved within the heat retentive heat conductive gel. When used to cool the breast, the moist heat foundation surface is generally not provided with water, although it could be if rapid and efficient cooling of the breast is desired.

In an alternative embodiment, heating or cooling of the heat retentive heat conducting material may be achieved by a thermochemical reaction, as is well known in the medical thermal pack art. An endothermic or an exothermic chemical reaction can be achieved by mixing two or more ingredients stored in sealed separate compartments until the moment of use. The endo- or exothermic nature of the reaction will provide, respectively, cold or heat. Mixing materials such as water and dry solid ammonium nitrate are well known in the thermal pack art to produce an endothermic reaction. Mixing materials such as water and dry solid calcium chloride are also well known in the medical thermal pack art for producing an exothermic reaction. The materials cited here for producing endo- or exo-thermic reactions are merely examples and are not intended to limit the number or kinds of materials useable to produce heat or cold or to limit the scope of the present invention, which scope will be readily understood by those skilled in the medical thermal pack art.

It is contemplated that the use of ingredients stored sealed separate compartments for use in producing heat or cold will comprise a one-use disposable embodiment of the present invention. In contrast, the embodiment in which the present invention is soaked in warm water for heat or refrigerated for cold is a re-useable embodiment.

Where ingredients must be mixed for heat or cold in a one-use embodiment, the ingredients would be stored within the cavity in the conformable C-shaped member. The user would have means to break the seal of the two or more ingredient compartment, thus allowing mixing of the heat or cold producing ingredients within the cavity of the C-shaped conforming member. Seal breaking means are exemplified, but not limited to, a manual action of bending or twisting the conformable member so as to break internal compartment seal allowing mixing of the heat-or-cold producing ingredients.

DESCRIPTION OF THE DRAWINGS

The present invention may best be described in conjunction with the accompanying drawings, in which.

DETAILED DESCRIPTION OF THE DRAWINGS

Figure 1:
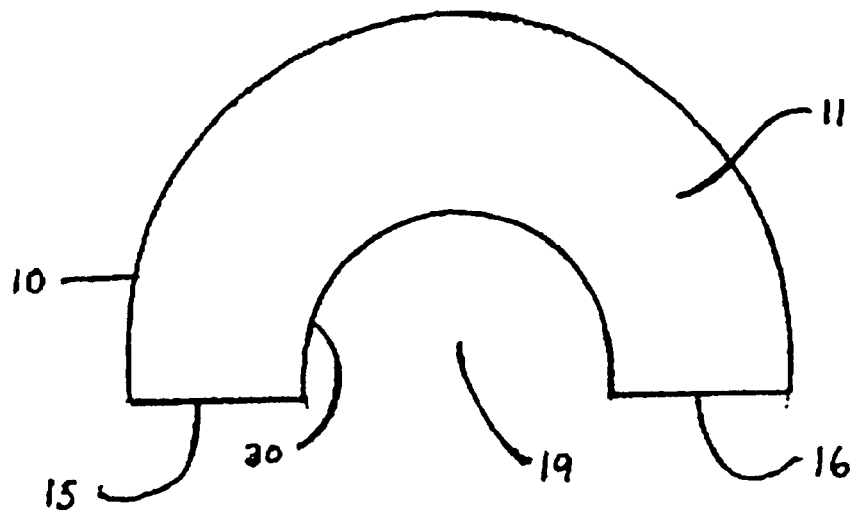
FIG. 1 is a top plan view of the thermal heat pack of the present invention.
Figure 2:
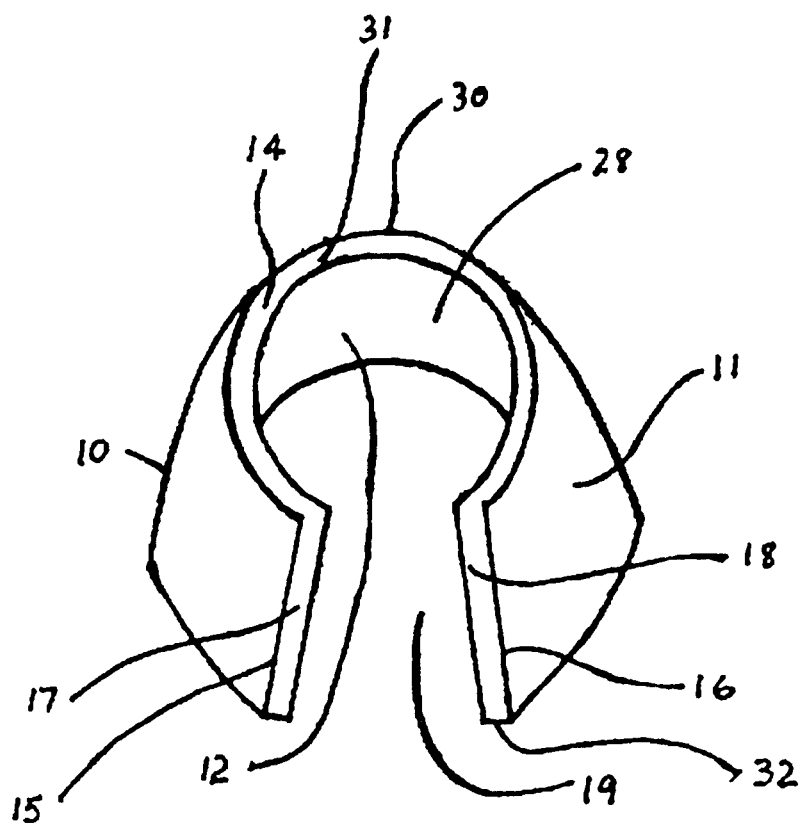
FIG. 2 is a perspective view of the thermal heat pack of FIG. 1, shown being bent.

As shown in FIGS. 1,2 and 4–7, the present invention includes a thermal heat pack, including a sealed generally flattened C-shaped conforming member 10, having top surface 11 corresponding to segmented bottom surface 12, upwardly extending circumferential edge wall 13, and end walls 17, 18 at edges 15, 16 of heat pack 10. End walls 17, 18 are separated by a space therebetween, such as recess 19 bounded by inner curved wall 30 extending parallel in a curved relationship with outer curved wall 32 of C-shaped member 10.

Therefore, thermal heat pack 10 includes hollow C-shaped member 10 with interior fluid flow chamber pocket 14, which pocket is between respective top surface 11, and respective bottom surface 12. Preferably interior fluid flow chamber pocket 14 includes a thermal conductive gel.

At their respective proximal ends, edges 15, 16 converge toward, and intersect with, common central recess portion 19 to create a hollow chamber for the even flow of viscous heat conducting material therethrough.

While central recess portion 19 may be a common point at which radially extending edges 15, 16 meet, in the preferred embodiment shown in FIGS. 1–2, and 4–7, recess portion 19 includes further centrally located recess 28, which further recess 28 is for a nipple to extend therethrough.

Recess 28 is bounded by curved edge 30 having edge wall 31 extending between top surface 11 and bottom surface 12 of heat pack 10.

Recess 19 permits flexible heat pack 10 to assume various sized domed shapes upon different sized female breasts, or other protruding body parts, since the movement of edge wall 17 of segment 14 toward edge wall 18 of heat pack 10 causes flat top 11 to move from a common plane in two dimensions to a dome shape of a plurality of intersecting planes in three dimensions.

Thus, when edges 15, 16 with walls 17, 18 extending therefrom are moved toward each other, heat pack 10 assumes a variable three-dimensional cup shape. For larger sized breasts, edges 15, 16, etc. are not moved completely together.

Recess 19 and centrally located recess 28 serves for placing the cylindrical conforming heat pack member 10 upon the breast, and for maintaining the configuration of C-shaped heat pack 10 relative to the corresponding contour of the breast, depending upon the desired size.

Heat pack 10 permits flow of the conventional heat conductive material, such as a heat imparting medium or a cooling medium, such as a gel fluid, throughout interior pocket 14, to insure even flow of the gel fluid and even distribution of the heat or coolness imparted to the afflicted breast.

Figure 8:
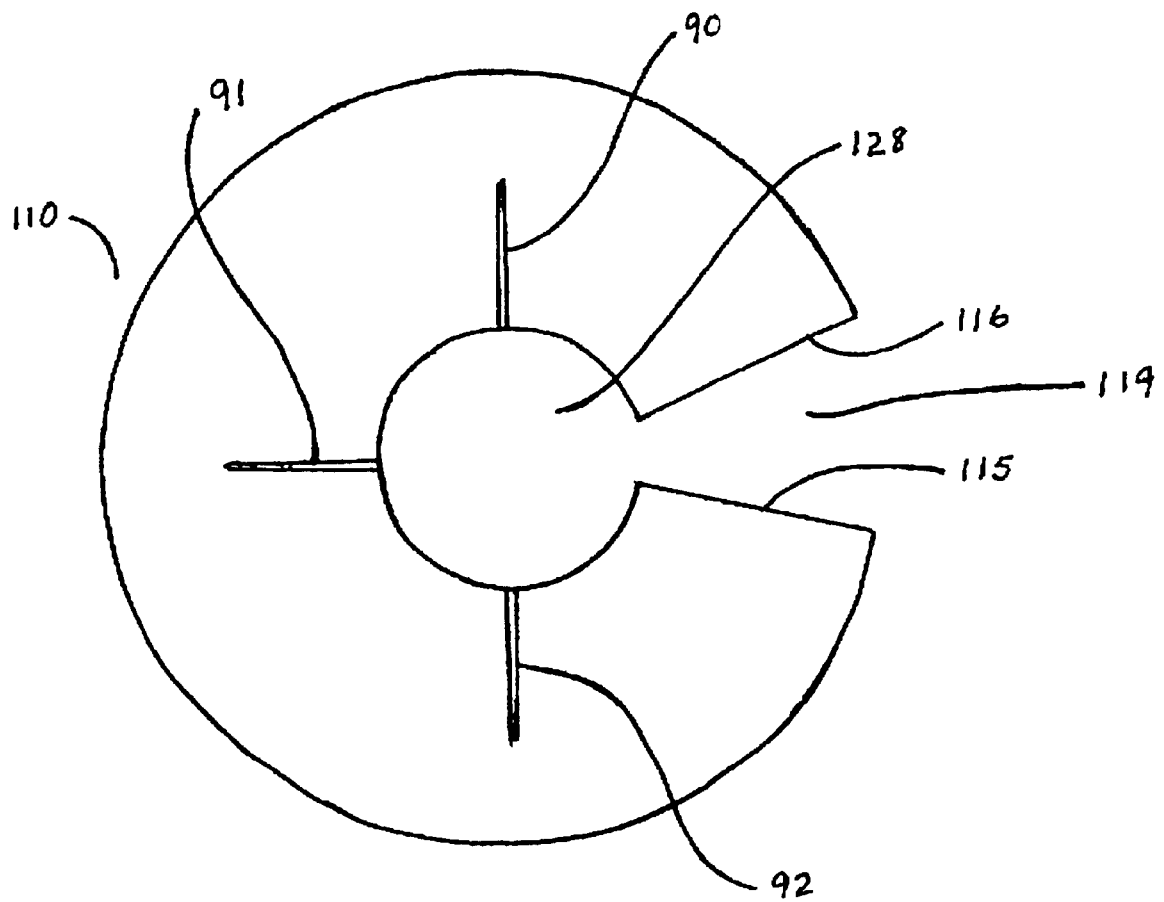
FIG. 8 is a top plan view of another embodiment with a narrower indentation and with slits.

As shown in the alternate embodiment shown in FIG. 8, because the narrow recess 119 leads to hole 128 between edges 115, 116 of heat pack 110, is preferably tapered, heat pack 110 assumes a generally domed cup shape 10.

As also shown in FIG. 8, the C-shaped thermal pack may have at least one cut out slit portions 90, 91, 92 around inner central recess 128. At least one slit may also be alternatively provided in the embodiments shown in FIGS. 1, 2 and 4–7, as well as FIG. 3.

Referring again to the preferred embodiment of FIGS. 1,2 and 4–7, thermal heat pack 10 includes foundation bottom member 12 which is placed removably adjacent against a breast. As is apparent, foundation bottom member 12, such as terry cloth, corresponds to the exact contour of the breast to provide a uniform heat across the breast. Further, thermal heat pack 10 flexes to adapt to accept the skin of the breast.

When in use, the C-shaped thermal heat pack 10 is placed against the breast with foundation bottom 12 placed against the breast. The flexible C-shaped thermal heat pack 10 flexes to the general shape of the breast to assist in keeping heat pack 10 in the desired position over the breast.

Various design modifications may be made to recess indentation so that it may be narrow as is recess indentation 119 in FIG. 8 or wide as in recess indentation 19 shown in FIG. 1.

Figure 3:
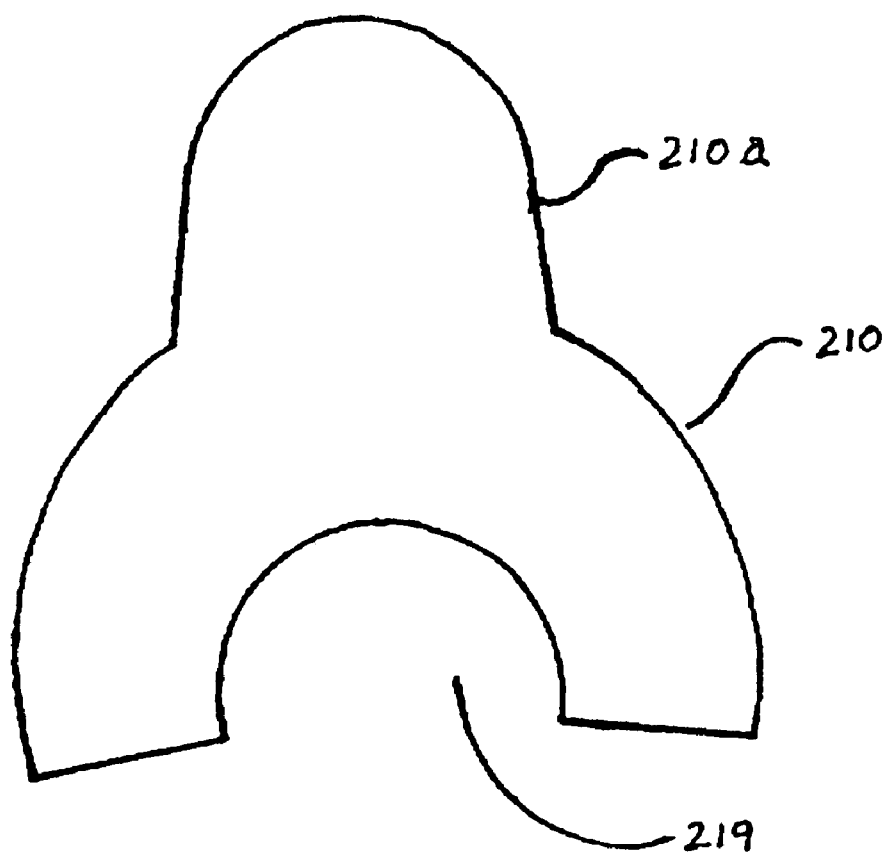
FIG. 3 is a top plan view of another embodiment of the thermal heat pack of the present invention with an appendage handle.
Figure 4:
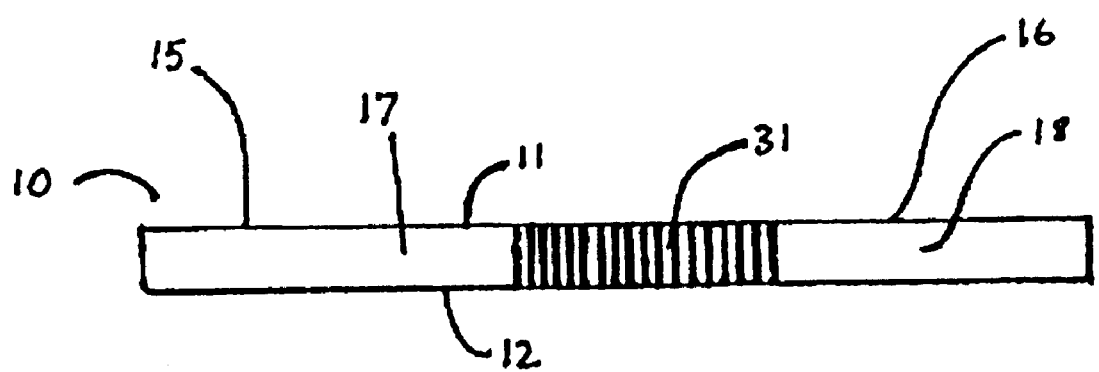
FIG. 4 is a front elevational view of the thermal heat pack as in FIG. 1.
Figure 5:
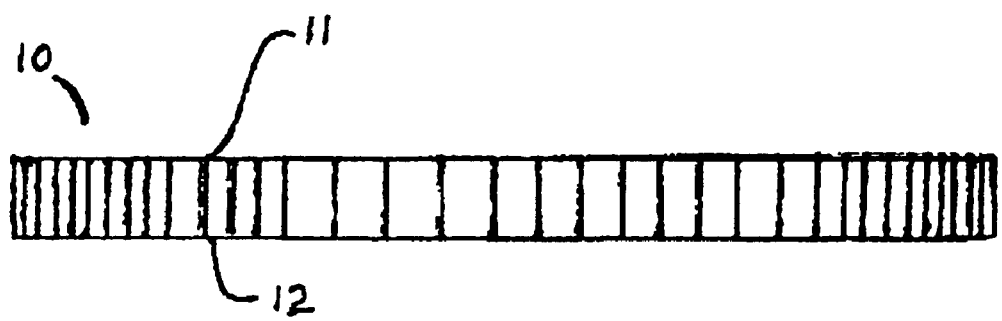
FIG. 5 is a rear elevational view of the thermal heat pack of the present invention as in FIG. 1.
Figure 6:
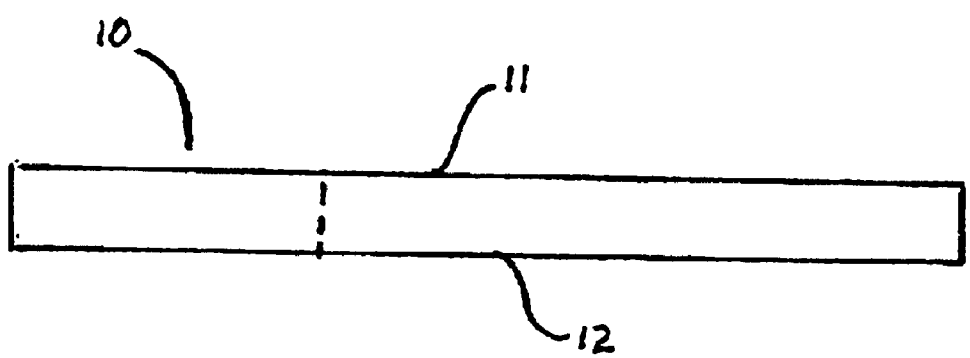
FIG. 6 is a left side elevational view of the heat pack as shown in FIG. 1.
Figure 7:
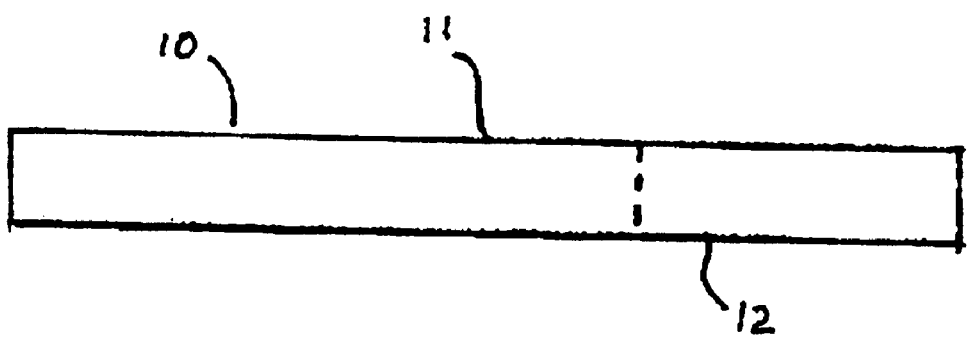
FIG. 7 is a right side elevational view of the heat pack of the present invention as in FIG. 1.

As shown in FIG. 3, appendage handle 210a may alternatively be provided to heat pack 210 to hold the heat pack on place upon the breast wherein appendage 210a is placed under the armpit of the user.

Figure 9:
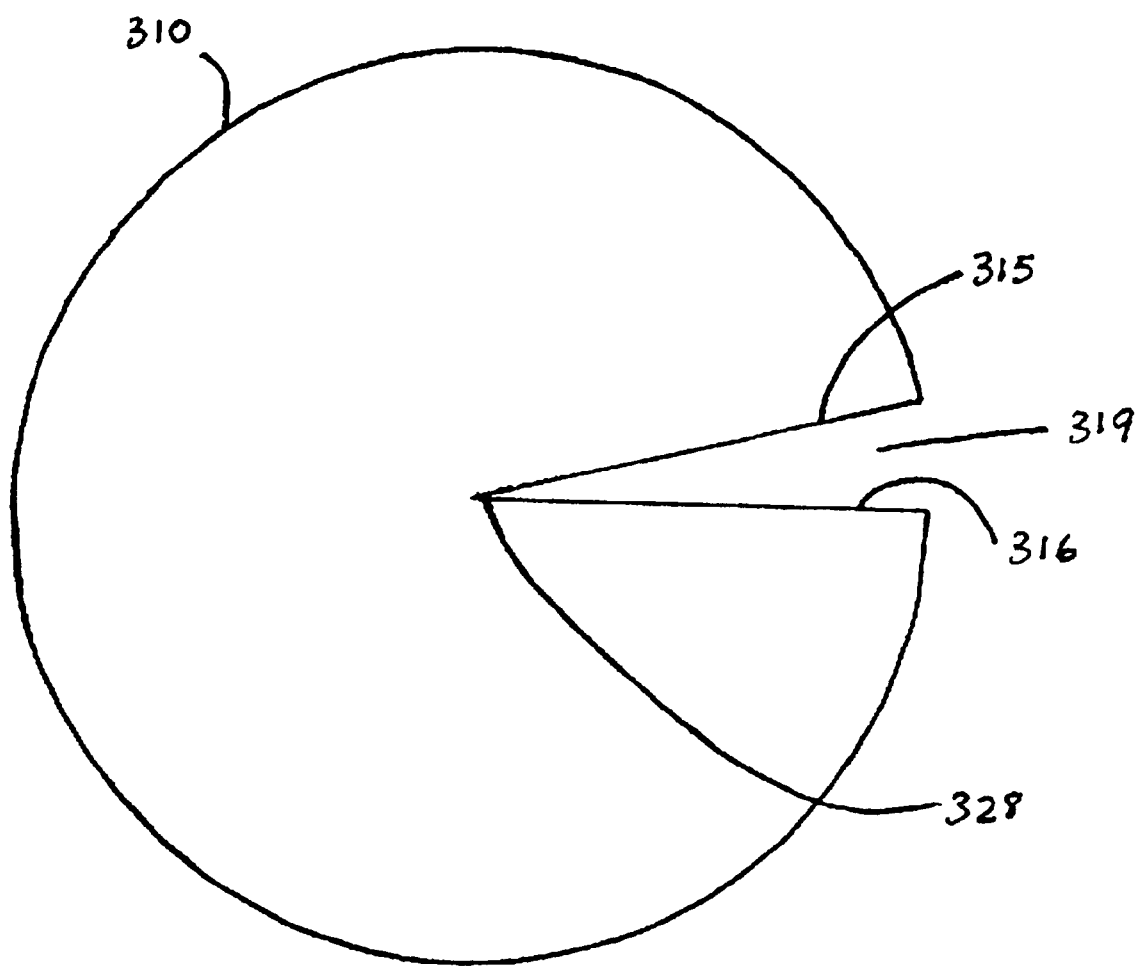
FIG. 9 is a top plan view of yet another embodiment.

As shown in FIG. 9, in a further alternate embodiment C-shaped heat pack 310 includes narrow indentation recess 19, which extends along tapered edges 315, 316 toward midpoint 328.

It is further anticipated that in certain circumstances recesses 19, 119, 219 or 319 may be covered by a web of a flexible material, such as cloth.

Figure 10:
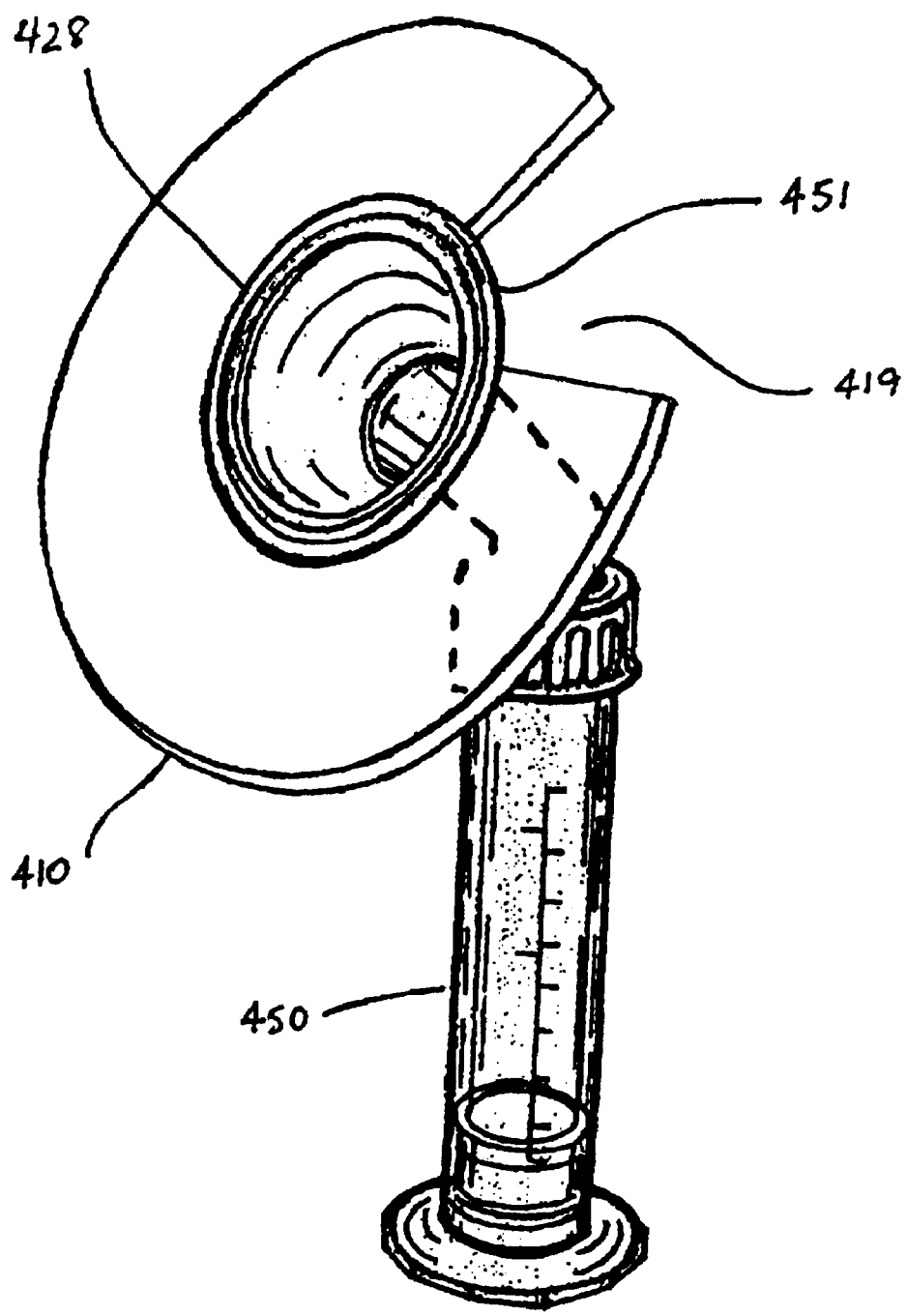
FIG. 10 is a perspective view of yet another embodiment used with a conventional breast pump; and, FIG. 11 is a heat pack as in FIG. 8 with an alternate nipple shield.

Other applications may be made to various other body parts other than the breast and the nipple where the body part constitutes a generally conical or angular protrusion, such as an elbow, knee, or an ankle. Furthermore, as shown in FIG. 10, C-shaped heat pack 410 may be used in combination with a conventional breast milk pump 450, wherein nipple funnel 451 is inserted within recess 419 to fit within centrally located further recess 428 of C-shaped heat pack 410.

Figure 11:
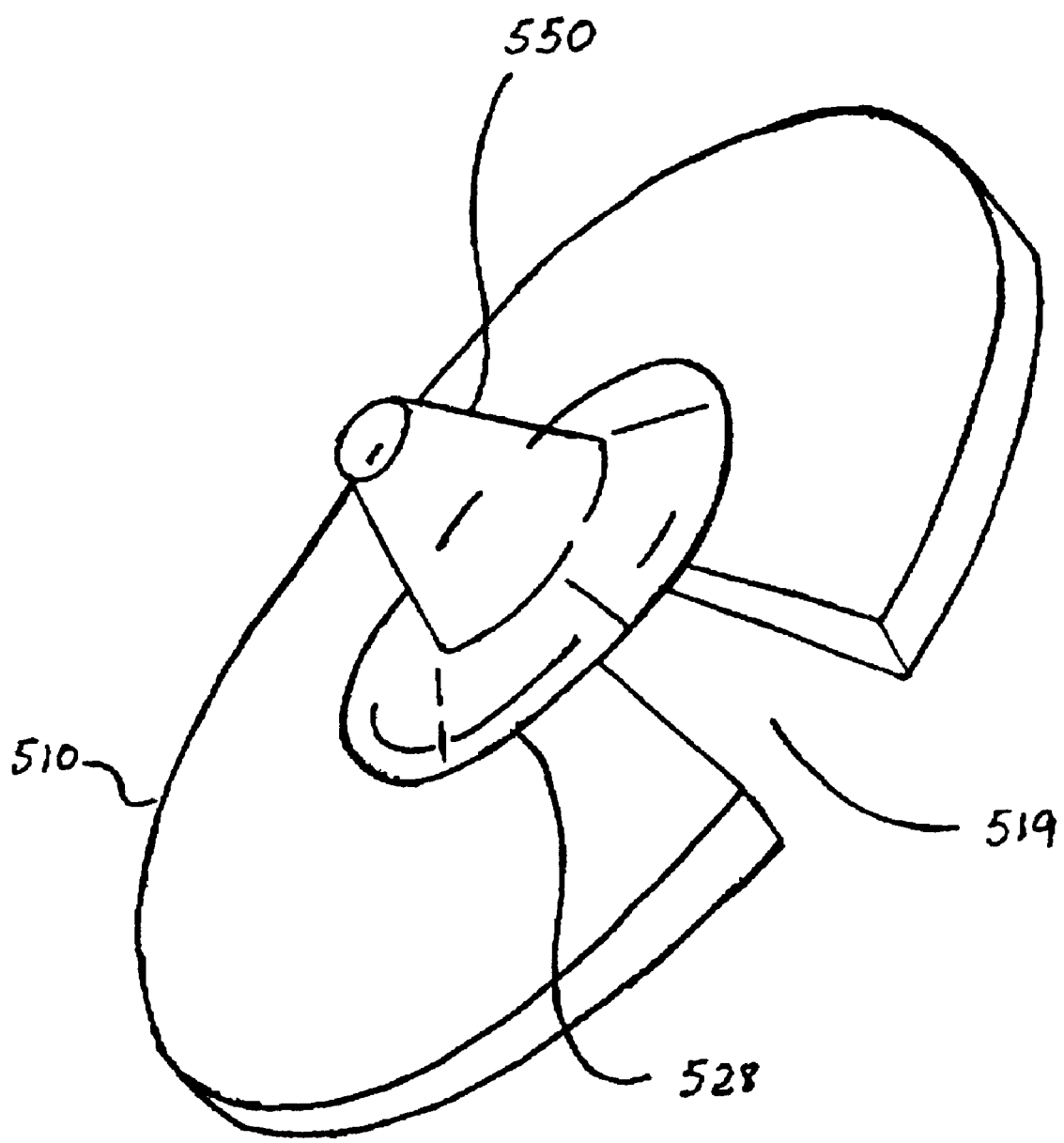

As shown in FIG. 11, C-shaped heat pack 510 may be used with a nipple shield cap 550, which is inserted within recess 519, to fit within centrally located further recess 428 of C-shaped heat pack 510.

Moreover, the pack may be applied in a flat position to any part of the body.

It is further assumed that other modifications may be made to the present invention, without departing from the spirit and scope of the present invention, as noted in the appended claims.

What is claimed is:

1. A thermal heat pack adapted to closely correspond to the contours sized female breasts to heat the adjacent skin area; said thermal heat pack comprising:

a generally C-shaped curved member having a pair of ends separated by a space therebetween;

a skin-facing bottom foundation surface forming one side of said thermal heat pack;

said curved portion having a central recess portion;

said curved member including pliant heat conducting material, said curved member being bendable from a flattened shape to a protruding shape corresponding to an outer contour of the female breast, wherein said curved member uniformly applies heat to said breast.

2. The heat pack as in claim 1 further comprising a fluid flow chamber therebetween for the circulation of the said pliant heat conducting material within said heat pack.

3. The thermal heat pack as in claim 1, wherein said heat conductive material is a heat imparting medium.

4. The thermal heat pack as in claim 1, wherein said heat conductive material is a cooling imparting medium.

5. The thermal heat pack as in claim 1, wherein said central portion further includes a further central recess portion.

6. The heat pack as in claim 1, wherein said curved member is bendable upon a breast receiving portion of a breast pump.

* * * * *

UNITED STATES PATENT AND TRADEMARK OFFICE
CERTIFICATE OF CORRECTION

PATENT NO.    : 6,261,313 B1
DATED         : May 15, 2001
INVENTOR(S)   : A. M. Heitmann et al.

It is certified that error appears in the above-identified patent and that said Letters Patent is hereby corrected as shown below:

Claim 32,
Line 2, delete ";" (semicolon) and substitute -- : -- (colon) in its place.

Claim 41,
Line 13, after "conduit" insert -- for --.

Signed and Sealed this

Twenty-sixth Day of March, 2002

Attest:

JAMES E. ROGAN
*Attesting Officer*     *Director of the United States Patent and Trademark Office*

UNITED STATES PATENT AND TRADEMARK OFFICE
CERTIFICATE OF CORRECTION

PATENT NO.    : 6,261,313 B1
DATED         : July 17, 2001
INVENTOR(S)   : John MacWhinnie et al.

It is certified that error appears in the above-identified patent and that said Letters Patent is hereby corrected as shown below:

This certificate supersedes Certificate of Correction issued March 26, 2002, the number was erroneously mentioned and should be deleted since no Certificate of Correction was granted.

Signed and Sealed this

Fourth Day of June, 2002

*Attest:*

*Attesting Officer*

JAMES E. ROGAN
*Director of the United States Patent and Trademark Office*